United States Patent [19]
Murayama et al.

[11] 3,940,363
[45] Feb. 24, 1976

[54] PIPERIDINE DERIVATIVES AND THEIR USE AS STABILIZERS

[75] Inventors: Keisuke Murayama; Syoji Morimura; Takao Yoshioka; Tomoyuki Kurumada, all of Hiro, Japan

[73] Assignee: Sankyo Company Limited, Japan

[22] Filed: July 19, 1973

[21] Appl. No.: 380,547

[30] Foreign Application Priority Data
July 27, 1972  Japan.............................. 47-75263

[52] U.S. Cl. 260/45.8 N; 260/45.75 N; 260/45.8 NZ; 260/293.63; 260/293.64; 260/294.8 G; 260/295 SP; 260/296 D
[51] Int. Cl.² .......................................... C08K 5/00
[58] Field of Search ................ 260/45.8 N, 45.8 NZ

[56] References Cited
UNITED STATES PATENTS

| | | | |
|---|---|---|---|
| 2,993,021 | 7/1961 | Bavley et al. .................. | 260/45.8 N |
| 3,329,645 | 7/1967 | Childers......................... | 260/45.8 N |
| 3,513,170 | 5/1970 | Murayama et al............. | 260/45.8 N |
| 3,560,433 | 2/1971 | Suzuki et al. .................. | 260/45.8 N |
| 3,640,928 | 2/1972 | Murayama et al............. | 260/45.8 N |
| 3,663,558 | 5/1972 | Murayama et al............. | 260/45.8 N |
| 3,708,488 | 1/1973 | Murayama et al............. | 260/45.8 N |
| 3,790,525 | 2/1974 | Murayama et al............. | 260/45.8 N |
| 3,840,494 | 10/1974 | Murayama et al............. | 260/45.8 N |

*Primary Examiner*—M. J. Welsh
*Attorney, Agent, or Firm*—Toren, McGeady and Stanger

[57] ABSTRACT

Piperidine derivatives having the formula

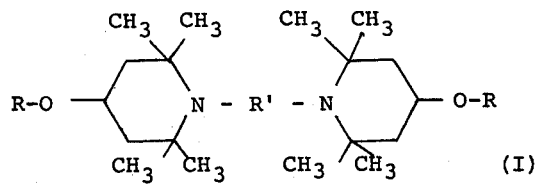

(I)

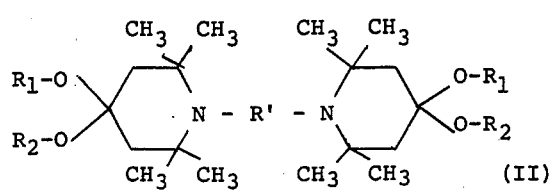

(II)

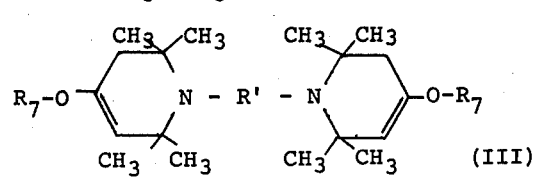

(III)

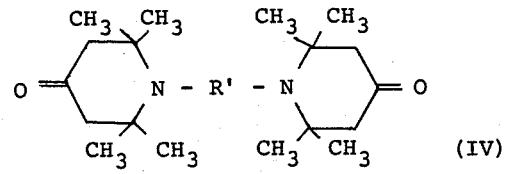

(IV)

wherein

R' represents an alkylene group which may be interrupted with an oxygen or sulfur atom, an alkenylene group, an alkynylene group, an aralkylene group, an aliphatic diacyl group, a group of the formula

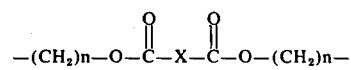

in which $n$ is an integer of 1 or 2 and X is an alkylene group, or *o*-, *m*- or *p*-phenylene group or the carbon atoms of CO groups may be directly joined in the absence of X or a group of the formula

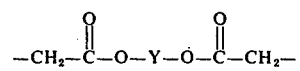

in which Y is an alkylene group or *O*-, *m*- or *p*-phenylene group;

R represents hydrogen atom, an alkyl group, a cycloalkyl group, an aralkyl group, an aryl group, an alkoxycarbonylalkenyl group, an aliphatic, aromatic or heterocyclic monoacyl group, a N-substituted carbamoyl group, a N-substituted thiocarbamoyl group or a monovalent radical derived from an oxoacid;

$R_1$ and $R_2$ individually represent a lower alkyl group or they jointly represent, together with the oxygen atoms, a group of the formula

[54]

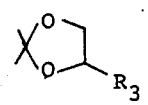

in which $R_3$ is hydrogen atom, a lower alkyl group or hydroxymethyl or a group of the formula

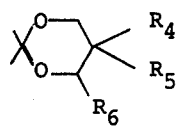

in which $R_4$ and $R_5$ may be the same or different and each represents hydrogen atom, a lower alkyl group or hydroxymethyl group and $R_6$ is hydrogen atom or a lower alkyl group; and $R_7$ represents an alkyl group or an aralkyl group.

They are prepared from the corresponding piperidine derivatives by the reaction with a halide R'—(Q)₂ wherein R' is as defined above and Q is a halogen atom and useful as stabilizers against photo- and thermal-deterioration of various synthetic polymers.

12 Claims, No Drawings

PIPERIDINE DERIVATIVES AND THEIR USE AS STABILIZERS

This invention relates to new piperidine derivatives and their use as stabilizers for synthetic polymers.

More particularly, it is concerned with a piperidine derivative selected from the group consisting of the compounds having the formula

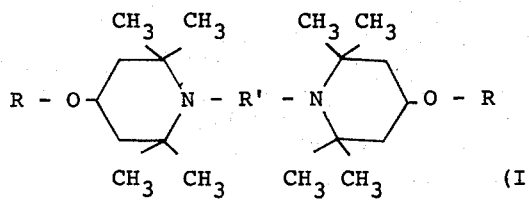

(I)

wherein

R' represents an alkylene group which may be interrupted with an oxygen or sulfur atom, an alkenylene group, an alkynylene group, an aralkylene group, an aliphatic diacyl group, a group of the formula $$-(CH_2)n-O-\overset{O}{\underset{\|}{C}}-X-\overset{O}{\underset{\|}{C}}-O-(CH_2)n-$$

in which n is an integer of 1 or 2 and X is an alkylene group, or o-, m- or p-phenylene group or the carbon atoms of CO groups may be directly joined in the absence of X or a group of the formula $$-CH_2-\overset{O}{\underset{\|}{C}}-O-Y-O-\overset{O}{\underset{\|}{C}}-CH_2-$$

in which Y is an alkylene group or o-, m- or p-phenylene group; and

R represents hydrogen atom, an alkyl group, a cycloalkyl group, an aralkyl group, an aryl group, an alkoxycarbonylalkenyl group, an aliphatic, aromatic or heterocyclic monoacyl group, a N-substituted carbamoyl group, a N-substituted thiocarbamoyl group or a monovalent radical derived from an oxoacid; the compounds having the formula

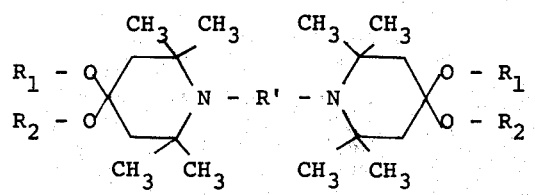

(II)

wherein

R' represents an alkylene group which may be interrupted with an oxygen or sulfur atom, an alkenylene group, an alkynylene group, an aralkylene group, an aliphatic diacyl group, a group of the formula

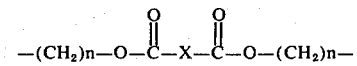

in which n is an integer of 1 or 2 and X is an alkylene group, or o-, m- or p-phenylene group or the carbon atoms of CO groups may be directly joined in the absence of X or a group of the formula

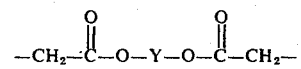

in which Y is an alkylene group or o-, m- or p-phenylene group;

$R_1$ and $R_2$ individually represent a lower alkyl group or they jointly represent, together with the oxygen atoms, a group of the formula

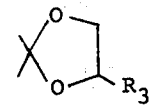

in which $R_3$ is hydrogen atom, a lower alkyl group or hydroxymethyl or a group of the formula

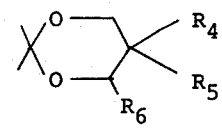

in which $R_4$ and $R_5$ may be the same or different and each represents hydrogen atom, a lower alkyl group or hydroxymethyl group and $R_6$ is hydrogen atom or a lower alkyl group; the compounds having the formula

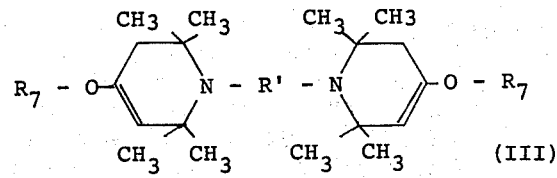

(III)

wherein

R' represents an alkylene group which may be interrupted with an oxygen or sulfur atom, an alkenylene group, an alkynylene group, an aralkylene group, an aliphatic diacyl group, a group of the formula

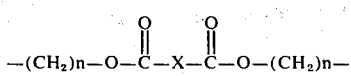

in which n is an integer of 1 or 2 and X is an alkylene group or o-, m- or p-phenylene group or the carbon atoms of CO groups may be directly joined in the absence of X or a group of the formula

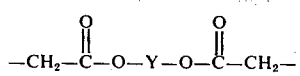

in which Y is an alkylene group or o-, m- or p-phenylene group; and $R_7$ represents an alkyl group or an aralkyl group; and the compounds having the formula

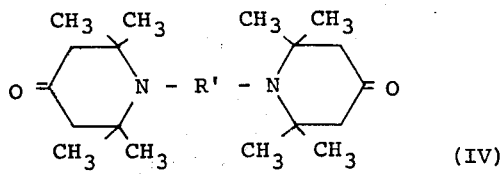

wherein

R' represents an alkylene group which may be interrupted with an oxygen or sulfur atom, an alkenylene group, an alkynylene group, an aralkylene group, an aliphatic diacyl group, a group of the formula

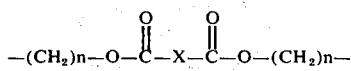

in which n is an integer of 1 or 2 and X is an alkylene group or o-, m- or p-phenylene group or the carbon atoms of CO groups may be directly joined in the absence of X or a group of the formula

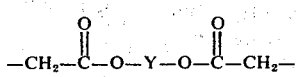

in which Y is an alkylene group or o-, m- or p-phenylene group.

Also, it is concerned with a synthetic polymer composition stabilized against photo- and thermal-deterioration wherein there is incorporated at least one of the piperidine derivatives of the above formulae (I), (II), (III) and (IV) in a sufficient amount to prevent such deterioration.

The term "synthetic polymer" as used herein is contemplated to include:

olefin, diene and styrene polymers including homopolymers of olefins, dienes and styrene (e.g., low and high density polyethylenes, polypropylene, polystyrene, polybutadiene and polyisoprene), and copolymers of olefins, dienes and styrene with each other or with other ethylenically-unsaturated monomers (e.g., ethylene-propylene copolymers, ethylene-butene copolymers, ethylene-vinyl acetate copolymers, styrene-butadiene copolymers and acrylonitrile-butadiene-styrene copolymers);

vinyl chloride and vinylidene chloride polymers including homopolymers of vinyl chloride and vinylidene chloride, vinyl chloride-vinylidene chloride copolymers, and copolymers of vinyl chloride or vinylidene chloride with vinyl acetate or other ethylenically-unsaturated monomers;

polyacetals e.g., polyoxymethylene and polyoxyethylene;

polyesters e.g., polyethylene terephthalate;

polyamides e.g., nylon-6, nylon-6,6 and nylon-6,10; and polyurethanes.

With respect to the R' in the above formulae (I) to (IV), the alkylene group, preferably of 1 to 6 carbon atoms, may be exemplified by methylene, ethylene, propylene, tetramethylene or hexamethylene or oxydiethyl [—(CH$_2$)$_2$—O—(CH$_2$)$_2$—] or thiodiethyl [—(CH$_2$)$_2$—S—(CH$_2$)$_2$—]; the alkenylene, preferably of 2 to 4 carbon atoms, by trans-2-butenylene; the alkynylene, preferably of 2 to 4 carbon atoms, by 2-butynylene; the aralkylene, preferably of 1 to 6 carbon atoms in the alkylene moiety, by p-xylene; the aliphatic diacyl group, preferably of 2 to 10 carbon atoms, by oxalyl, malonyl, succinoyl, adipoyl, sebacoyl or fumaroyl; etc.

With respect to the R in the above formula (I), the alkyl group, preferably of 1 to 18 carbon atoms, may be exemplified by methyl, ethyl, n-butyl, tert.-butyl, n-hexyl, octyl or stearyl; the cycloalkyl group, preferably of 5 or 6 carbon atoms, by cyclopentyl or cyclohexyl; the aralkyl group preferably of 1 or 2 carbon atoms in the alkyl moiety, by benzyl or phenethyl; the aryl group, preferably of 6 – 10 carbon atoms in the aryl moiety and with optional substituent(s), by phenyl, o-, m- or p-tolyl, naphthyl; the alkoxycarbonyl-alkenyl group preferably of 1 to 3 carbon atoms in the alkoxy moiety and of 2 to 4 carbon atoms in the alkenyl moiety, by 2-methoxycarbonylisipropenyl, 3-butoxycarbonylpropenyl or 4-methoxycarbonyl-1-butenyl; the aliphatic monoacyl group, preferably of 2 to 18 carbon atoms, by acetyl, butyryl, octanoyl, dodecanoyl, β-butylthiopropionyl, acryloyl, methacryloyl, crotonoyl or cyclohexanoyl; the aromatic monoacyl group, preferably with optional substituent(s), by benzoyl, o-, m- or p-chlorobenzoyl, o-, m- or p-hydroxybenzoyl, o-, m- or p-toluoyl, p-tert.butylbenzoyl or α- or β-naphthoyl; the heterocyclic monoacyl group by nicotinoyl, furoyl; the N-substituted carbamoyl group, preferably with substituent(s) of $C_1$–$C_4$ alkyl, cyclohexyl, phenyl or naphthyl by N-methyl-, N-butyl-, N-cyclohexyl-, N-phenyl-, N-α-naphthyl-carbamoyl; the N-substituted thiocarbamoyl group, preferably with substituent(s) of $C_1$–$C_4$ alkyl or phenyl, by N-methyl-, N-butyl- or N-phenyl-thiocarbamoyl; and the oxoacid yielding the corresponding monovalent radical by an unsubstituted or substituted sulfinic acid, e.g., benzenesulfinic acid, an unsubstituted or substituted sulfonic acid, e.g., benzenesulfonic acid, p-toluenesulfonic acid or methanesulfonic acid, an unsubstituted or substituted phosphoric acid, e.g., diphenylphosphoric acid, an unsubstituted or substituted phosphorous acid, e.g., diphenylphosphorous acid, an unsubstituted or substituted phosphonic acid, e.g., phosphonic acid and an unsubstituted or substituted boric acid, e.g., boric acid.

With respect to the $R_1$ and $R_2$ in the above formula (II), the lower alkyl group, preferably of 1 to 4 carbon atoms, may be exemplified by methyl, ethyl, propyl or butyl and the $R_1$ and $R_2$ may form quently tend to deteriorate and become colored by the action of light and heat together with elimination of hydrogen chloride therefrom. Polyamides are also frequently subjected to photo-deterioration. For the purpose of stabilizing these synthetic polymers against such deterioration, there have heretofore been proposed in the art a number of stabilizers; for example, for polyolefins, benzotriazole compounds and benzophenone compounds; for polyurethanes, phenol compounds and benzophenone compounds; and for polyvinyl chloride and polyvinylidene chloride, lead salts such as basic lead silicate and tribasic lead maleate, and organotin compounds such as dibutyltin laurate and dibutyltin maleate.

Although such prior stabilizers are believed to be considerably satisfactory, some problems to be im-

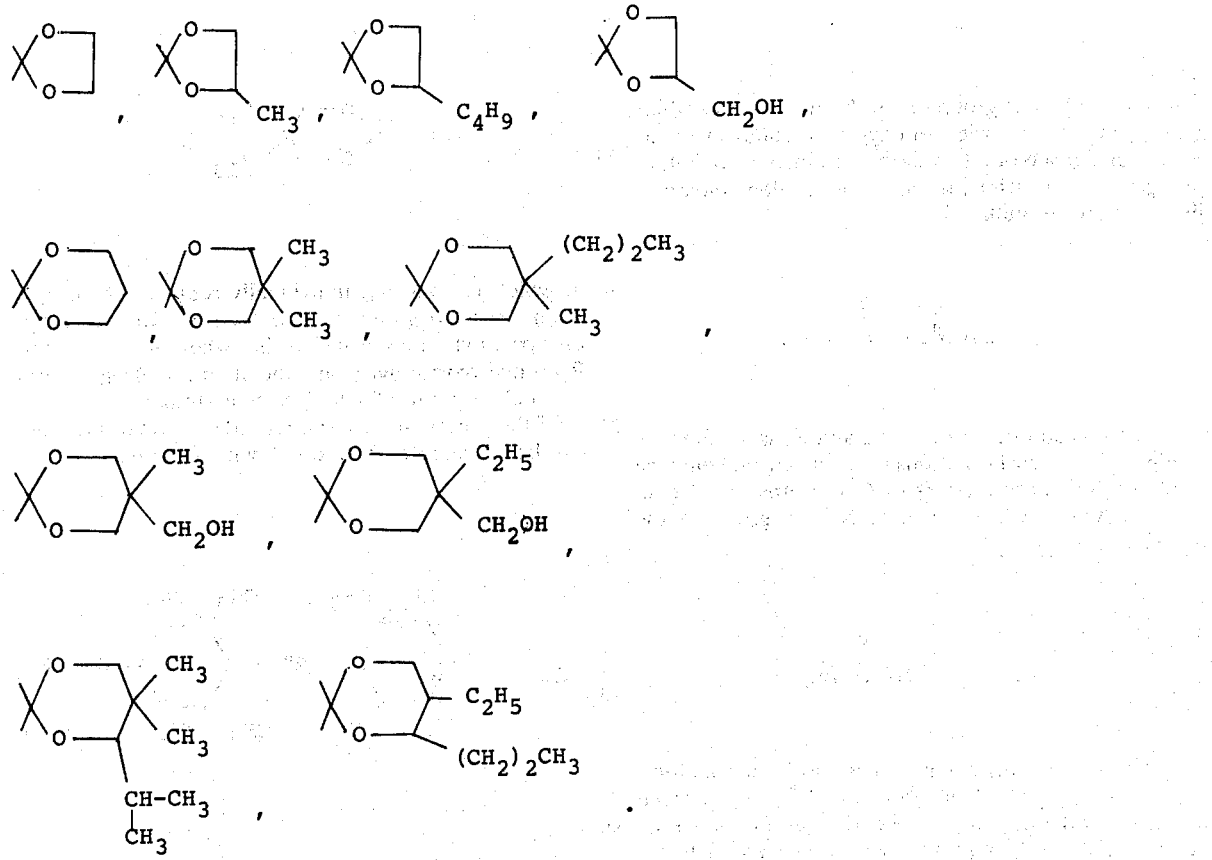

With respect to the $R_7$ in the above formula (III), the alkyl group, preferably of 1 to 18 carbon atoms, may be exemplified by methyl, propyl, pentyl, octyl, decyl or stearyl and the aralkyl group, preferably of 6 carbon atoms in the aryl moiety and of 1 or 2 carbon atoms in the alkyl moiety, may be benzyl or phenethyl.

Synthetic polymers have been widely utilized in the art, in view of their excellent properties, in various forms or shapes, for example, filament, fibre, yarn, film, sheet, other molded article, latex and foam. However, these polymers have some drawbacks such as poor light- and heat-stabilities and the like. Stated illustratively, polyolefins and polyurethane elastomers frequently tend to undergo severe deterioration when exposed to light such as sunlight or ultraviolet ray, and polyvinyl chloride and polyvinylidene chloride freproved still remain.

Thus, numerous attempts have been made in the art to find and develop new and more effective stabilizers.

As a result of our extensive studies to find a new type of stabilizers, it has been found that the new piperidine derivatives of the formulae (I), (II), (III) and (IV), exhibit a high stabilizing effect against photo- and thermal-deterioration of the synthetic polymers.

It is accordingly an object of this invention to provide the new piperidine derivatives (I), (II), (III) and (IV) having practical utility as stabilizers for the synthetic polymers.

Another object of this invention is to provide a synthetic polymer composition stabilized against the deterioration thereof by having incorporated therein, in a sufficient amount to prevent such deterioration, at least one of the piperidne derivatives (I), (II), (III) and (IV).

Other object of this invention will become apparent from the following description.

In one aspect of this invention, there is provided new groups of the piperidine derivatives (I), (II), (III) and (IV).

Of the piperidine derivatives (I), a preferable class can be represented by the following formula:

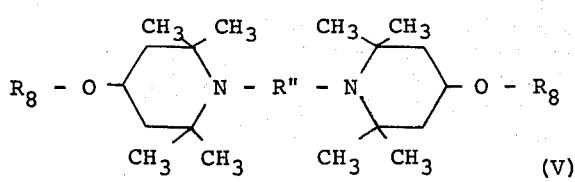

(V)

wherein

R'' is an alkylene group of 1 to 6 carbon atoms which may be interrupted with an oxygen or sulfur atom, an alkenylene group of 2 to 4 carbon atoms, an aralkylene group of 1 to 6 carbon atoms in the alkylene moiety, a group of the formula

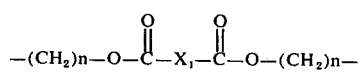

in which n is an integer of 1 or 2 and $X_1$ is an alkylene group of 1 to 6 carbon atoms or o-, m- or p-phenylene group or the carbon atoms of CO groups may be directly joined in the absence of X or a group of the formula

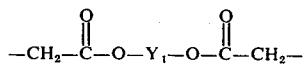

in which $Y_1$ is an alkylene group of 1 to 6 carbon atoms or o-, m- or p-phenylene group; and $R_8$ is hydrogen atom, an alkyl group of 1 to 18 carbon atoms, an alkoxycarbonylalkenyl group of 1 to 3 carbon atoms in the alkoxy moiety and of 2 to 4 carbon atoms in the alkenyl moiety, an aliphatic acyl group of 2 to 18 carbon atoms or a benzoyl group which may be substituted with halogen, hydroxy or alkyl of 1 to 3 carbon atoms.

Of the piperidine derivatives (II), a preferable class can be represented by the following formula

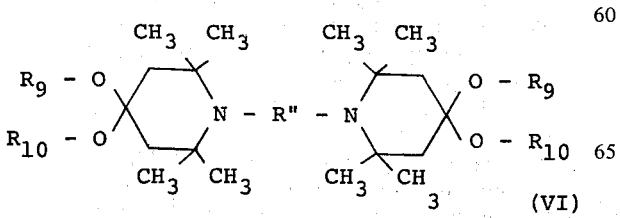

(VI)

wherein

R'' is as defined above; $R_9$ and $R_{10}$ individually represent an alkyl group of 1 to 4 carbon atoms or they jointly represent, together with the oxygen atoms, a group of the formula

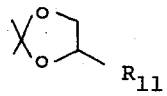

in which $R_{11}$ is hydrogen atom, an alkyl group of 1 to 4 carbon atoms or hydroxymethyl group or a group of the formula

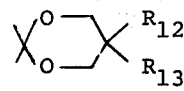

in which $R_{12}$ and $R_{13}$ individually represent hydrogen atom, an alkyl group of 1 to 4 carbon atoms or hydroxymethyl group provided that when one of $R_{12}$ and $R_{13}$ is hydroxymethyl group, the other is hydrogen atom or an alkyl group of 1 to 4 carbon atoms.

Of the piperidine derivatives (III), a preferable class can be represented by the following formula:

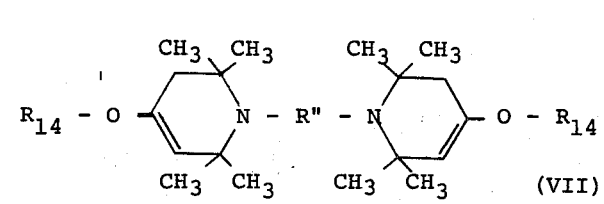

(VII)

wherein

R'' is as defined above and $R_{14}$ is an alkyl group of 1 to 18 carbon atoms or a phenylalkyl group of 1 or 2 carbon atoms in the alkyl moiety.

Of the piperidine derivatives (IV), a preferable class can be represented by the following formula:

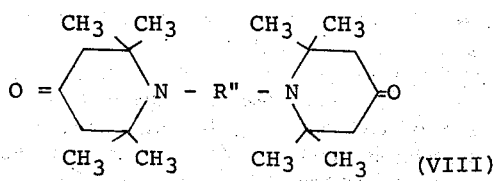

(VIII)

wherein R'' is as defined above.

Representatives of the piperidine derivatives (I), (II), (III) or (IV) of this invention are illustratively given below.

| Compound No. | Chemical Name |
|---|---|
| 1) | 1,2-Bis(4-benzoyloxy-2,2,6,6-tetramethyl-piperidino)ethane |
| 2) | 1,2-Bis[4-(β-methoxycarbonylisopropenyloxy)-2,2,6,6-tetramethylpiperidino]ethane |
| 3) | 1,6-Bis[4-benzoyloxy-2,2,6,6-tetramethyl-piperidino) hexane |
| 4) | α,α'-Bis(4-benzoyloxy-2,2,6,6-tetramethyl-piperidino)-p-xylene |
| 5) | 2,2'-Bis(2,2,6,6-tetramethyl-4-stearoyloxy-piperidino)diethylether |
| 6) | 2,2'-Bis[4-(2-furoyloxy)-2,2,6,6-tetramethyl-piperidino]diethylether |
| 7) | 2,2'-Bis(2,2,6,6-tetramethyl-4-p-tosyloxy-piperidino)diethylether |
| 8) | α,α'-Bis(2,2,6,6-tetramethyl-4-nicotinoyloxy-piperidino)-p-xylene |
| 9) | 1,4-Bis(4-benzoyloxy-2,2,6,6-tetramethyl-piperidino)-trans-2-butene |
| 10) | 1,4-Bis[2,2,6,6-tetramethyl-4-(N-phenyl-carbamoyloxy)piperidino]-2-butyne |
| 11) | Bis(4-acetoxy-2,2,6,6-tetramethyl)-1,1'-succinoylpiperidine |
| 12) | Bis(4-acetoxy-2,2,6,6-tetramethyl)-1,1'-adipoylpiperidine |
| 13) | Bis(4-methoxy-2,2,6,6-tetramethyl)-1,1'-fumaroylpiperidine |
| 14) | α,α'-Bis(4-hydroxy-2,2,6,6-tetramethyl-piperidino)-p-xylene |
| 15) | Bis[-(4-benzoyloxy-2,2,6,6-tetramethyl-piperidino)ethyl]succinate |
| 16) | Ethylene bis(4-benzoyloxy-2,2,6,6-tetramethyl-piperidinoacetate) |
| 17) | Bis[β-(4-benzoyloxy-2,2,6,6-tetramethyl-piperidino)ethyl]oxalate |
| 18) | Bis[β-(4-benzoyloxy-2,2,6,6-tetramethyl-piperidino)ethyl]terephthalate |
| 19) | N,N'-Hexamethylene-bis(8-aza-7,7,9,9-tetramethyl-1,4-dioxa-spiro[4.5]decane) |
| 20) | N,N'-Octamethylene-bis(8-aza-7,7,9,9-tetramethyl-1,4-dioxa-spiro[4.5]decane) |
| 21) | N,N'-Decamethylene-bis(8-aza-7,7,9,9-tetramethyl-1,4-dioxa-spiro[4.5]decane) |
| 22) | Ethylene bis(8-aza-7,7,9,9-tetramethyl-1,4-dioxa-spiro[4.5]-8-decylacetate) |
| 23) | N,N'-[adipoyl-bis(β-oxyethyl)]-bis(8-aza-7,7,9,9-tetramethyl-1,4-dioxa-spiro[4.5]decane) |
| 24) | N,N'-[terephthaloyl-bis(β-oxyethyl)]-bis(8-aza-7,7,9,9-tetramethyl-1,4-dioxa-spiro-[4.5]decane) |
| 25) | N,N'-(α,α'-p-xylylene)-bis(8-aza-7,7,9,9-tetramethyl-1,4-dioxa-spiro[4.5]decane) |
| 26) | N,N'(α,α'-p-xylylene)-bis(8-aza-2,7,7,9,9-tetramethyl-1,4-dioxa-spiro[4.5]decane) |
| 27) | N,N'-Hexamethylene-bis(8-aza-2-hydroxy-methyl-7,7,9,9-tetramethyl-1,4-dioxa-spiro[4.5]decane) |
| 28) | N,N'(α,α'-p-xylylene)-bis(8-aza-2-hydroxymethyl-7,7,9,9-tetramethyl-1,4-dioxa-spiro[4.5]decane) |
| 29) | N,N'-(α,α'-xylylene)-bis(9-aza-8,8,10,10-tetramethyl-1,5-dioxa-spiro[5.5]undecane) |
| 30) | N,N'(α,α'-p-xylylene)-bis(9-aza-3,3,8,8,10,10-hexamethyl-1,5-dioxa-spiro[5.5]-undecane) |
| 31) | N,N'-Ethylene-bis(9-aza-3-hydroxymethyl-3,8,8,10,10-pentamethyl-1,5-dioxa-spiro-[5.5]undecane) |
| 32) | N,N'-Hexamethylene-bis(9-aza-3-hydroxy-methyl-3,8,8,10,10-pentamethyl-1,5-dioxa-spiro[5.5]undecane) |
| 33) | N,N'-(α,α'-p-xylylene)-bis(9-aza-3-ethyl-3-hydroxymethyl-8,8,10,10-tetramethyl-1,5-dioxa-spiro[5.5]undecane) |
| 34) | N,N'-(α,α'-p-xylylene)-bis(9-aza-3-ethyl-8,8,10,10-tetramethyl-1,5-dioxa-2-propyl-spiro[5.5]undecane) |
| 35) | α,α'-Bis(4,4-dimethoxy-2,2,6,6-tetramethyl-piperidino)-p-xylene |
| 36) | α,α'-Bis(2,2,6,6-tetramethyl-4-methoxy-Δ³-dehydropiperidino)-p-xylene |
| 37) | α,α'-Bis(2,2,6,6-tetramethyl-4-octyloxy-dehydropiperidino)-p-xylene |
| 38) | α,α'-Bis(2,2,6,6-tetramethyl-4-octadecyloxy-Δ³-dehydropiperidino)-p-xylene |
| 39) | α,α'-Bis(4-benzyloxy-2,2,6,6-tetramethyl-Δ³-dehydropiperidino)-p-xylene |
| 40) | 1,6-Bis(2,2,6,6-tetramethyl-4-oxopiperidino)-hexane |
| 41) | 1,8-Bis(2,2,6,6-tetramethyl-4-oxopiperidino)-octane |
| 42) | 1,10-Bis(2,2,6,6-tetramethyl-4-oxopiperidino)-decane |
| 43) | α,α'-Bis(2,2,6,6-tetramethyl-4-oxopiperidino)-p-xylene |
| 44) | Ethylene bis(2,2,6,6-tetramethyl-4-oxo-piperidino-acetate) |
| 45) | Bis(2,2,6,6-tetramethyl-4-oxo-β-piperidino-ethyl)terephthalate |
| 46) | Bis(2,2,6,6-tetramethyl-4-oxo-β-piperidino-ethyl)adipate |

Of the above illustrated piperidine derivatives, more preferable are those compounds as indicated by the above Compound Nos. 1, 4, 5, 9, 14, 19, 22, 24, 27, 30 and 40.

The piperidine derivatives (I), (II), (III) and (IV) of this invention are all new substances and they may be readily prepared, for instance, according to the procedures as shown below, respectively.

A. The piperidine derivatives (I) are prepared by reacting the starting compounds (IX) with the halide (X) as illustrated by the following reaction schema:

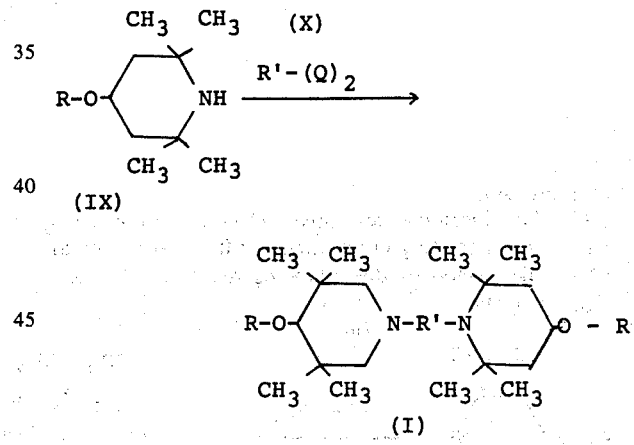

In the above formulae, R and R' are as defined above and Q is a halogen atom. The reaction may be advantageously effected in the absence or presence of an inert organic solvent, such as an aromatic hydrocarbon, e.g., benzene, toluene or xylenes or a dialkylformamide, e.g., dimethylformamide. The starting compound (IX) may be preferably used in this reaction in an amount of 2 moles to the reagent. The reaction temperature is not critical, but it is usually a reflux temperature of the solvent, if employed. The reaction period of time is also not critical, but the reaction is usually completed in about 1 to about 14 hours. The reaction may be advantageously effected in the presence of an acid binding agent. The acid binding agent may be any of those commonly employed in the art and examples of such agents may include inorganic bases, e.g., sodium carbonate, potassium carbonate, sodium hydroxide or potassium hydroxide and organic bases, e.g., trimethylamine or triethanolamine. The desired product may be easily recovered and purified by a conventional method.

B. The piperidine derivatives (II) are prepared by reacting the starting compounds (XI) with the halide (X) as illustrated by the following reaction schema:

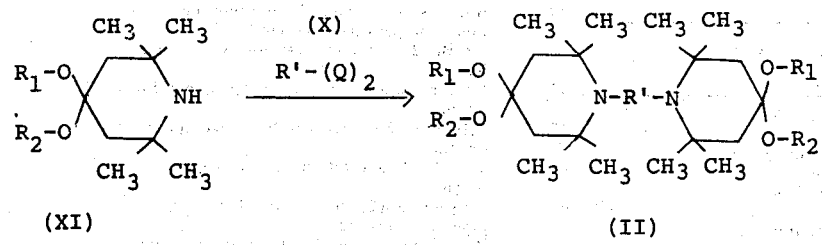

In the above formulae, $R_1$, $R_2$, $R'$ and Q are as defined above. The reaction conditions in this reaction may be the same as set forth above with respect to the method (A).

C. The piperidine derivatives (III) are prepared by reacting the starting compounds (XII) with the halide (X) as illustrated by the following reaction schema:

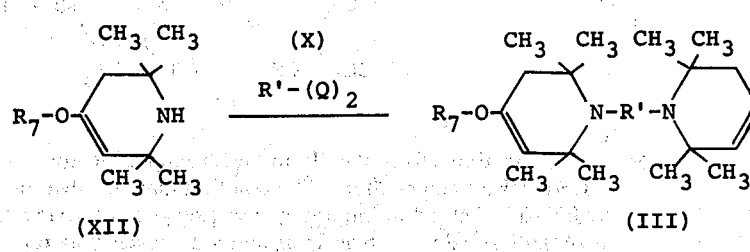

In the above formulae, $R_7$, $R'$ and Q are as defined above. The reaction conditions in this reaction may be the same as set forth above with respect to the method (A).

D. The piperidine derivatives (IV) are prepared by reacting the starting compounds (XIII) with the halide (X) as illustrated by the following reaction schema:

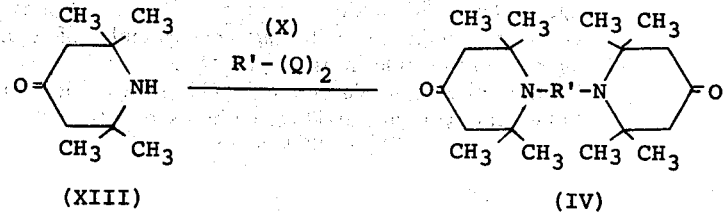

In the above formulae, $R'$ and Q are as defined above. The reaction conditions in this reaction may be the same as set forth above with respect to the method (A).

Alternatively, the piperidine derivatives (IV) may be obtained starting from the piperidine derivatives (II).

Thus, the piperidine derivatives (IV) can be, as illustrated below, prepared from the piperidine derivatives (II) through hydrolysis with an acid.

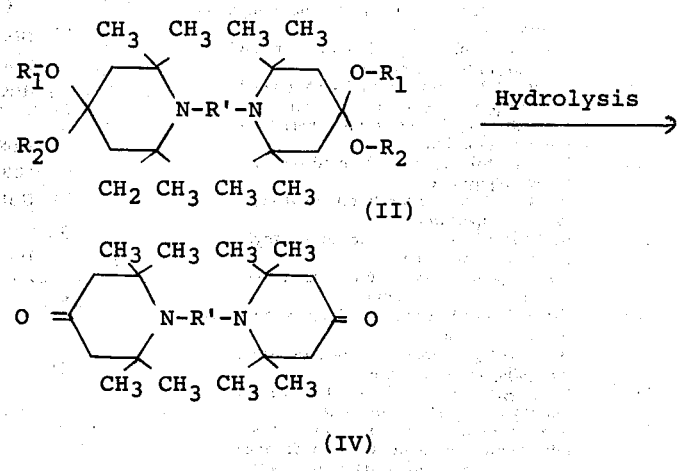

In the above formulae, $R_1$, $R_2$ and $R'$ are as defined above. This alternative reaction may be effected according to the procedure commonly utilized in the art for hydrolysis with an acid. The reaction may be conducted by intimately contacting the starting compounds (II) with the acid, preferably in its aqueous solution form. The reaction temperature is not critical, but it is usually room temperature or a temperature kept under ice-cooling. The reaction period of time is not also critical, but the hydrolysis is usually completed in about 1 - 60 minutes. Examples of the acid which may be employed include mineral acids, e.g., hydrochloric, sulfuric or phosphoric acid, organic acids being optionally employed. The desired product may be readily recovered and purified by a conventional method, for instance, by neutralization with a suitable alkali, extraction with a suitable organic solvent, e.g., benzene or n-hexane followed by removal of the solvent through distillation.

In another aspect of this invention, there is provided a synthetic polymer composition stabilized against photo- and thermal-deterioration thereof wherein there is incorporated, in a sufficient amount to prevent such deterioration, at least one of the piperidine derivatives (I), (II), (III) and (IV).

The amount of the stabilizing compound or compounds of formula (I), (II), (III) or (IV) needed for effective stabilization of the synthetic polymer will depend on a variety of factors, such as the type and properties of the polymer concerned, its intended use, and the presence of other stabilizers. It is generally satisfactory to use from 0.01 % to 5.0 % by weight of the stabilizing compounds, based on the weight of the synthetic polymer, but the most effective range will vary with the type of polymer — viz. 0.01 % to 2.0 %, preferably 0.02 % to 1.0 %, by weight for olefin, diene and styrene polymers; 0.01 % to 1.0 %, preferably 0.02 % to 0.5 %, by weight for vinyl chloride and vinylidene chloride polymers; and 0.01 % to 5.0 %, preferably 0.02 % to 2.0 %, by weight for polyurethanes and polyamines. If desired, two or more of the compounds of the invention may be used together.

The stabilizers of the invention may readily be incorporated into the synthetic polymers by conventional techniques, at any convenient atage prior to the manufacture of shaped articles therefrom. For example, the stabilizer may be mixed with the synthetic polymer in dry powder form, or a suspension or emulsion of the stabilizer may be mixed with a solution, suspension or emulsion of the synthetic polymer.

The stabilized synthetic polymer compositions of the invention may also contain various conventional additives.

Examples of such additives are illustratively shown below.

Antioxidants

Simple 2,6-dialkylphenols, such as, for example, 2,6-di-tert.butyl-4-methylphenol, 2-tert.butyl-4,6-dimethylphenol, 2,6-di-tert.butyl-4-methoxy-methylphenol and 2,6-dioctadecyl-4-methylphenol.

Derivatives of alkylated hydroquinones, such as, for example, 2,5-di-tert.butyl-hydroquinone, 2,5-di-tert.amyl-hydroquinone, 2,6-di-tert.butyl-hydroquinone, 2,5-di-tert.butyl-4-hydroxyanisole, 3,5-di-tert.butyl-4-hydroxyanisole and tris(3,5-di-tert.butyl-4-hydroxyphenyl)phosphite, 3,5-di-tert.butyl-4-hydroxyphenyl-stearate, di-(3,5-di-tert.butyl-4-hydroxyphenyl)adipate.

Hydroxylated thiodiphenyl ethers, such as, for example, 2,2'-thiobis(6-tert.butyl-4-methylphenol), 2,2'-thiobis(4-octylphenol), 4,4'-thiobis(6-tert.butyl-3-methylphenol), 4,4'-thiobis(3,6-di-sec.amylphenol) and 4,4'-thiobis(6-tert.butyl-2-methylphenol), 4,4'-Bis(2,6-dimethyl-4-hydroxyphenyl)disulfide.

Alkylidene-bisphenols, such as, for example, 2,2'-methylene-bis(6-tert.butyl-4-methylphenol), 2,2'-methylene-bis(6-tert.butyl-4-ethylphenol), 4,4'-methylene-bis(6-tert.butyl-2-methylphenol), 4,4'-methylene-bis(2,6-di-tert.butylphenol), 2,6-di-(3-tert.butyl-5-methyl-2-hydroxybenzyl)-4-methylphenol, 2,2'-methylene-bis[4-methyl-6-($\alpha$-methylcyclohexyl)-phenol], 1,1-bis(3,5-dimethyl-2-hydroxyphenyl)-butane, 1,1-bis(5-tert.butyl-4-hydroxy-2-methylphenyl)-butane, 2,2-bis(5-tert.butyl-4-hydroxy-2-methylphenyl)butane, 2,2-bis(3,5-di-tert.butyl-4-hydroxyphenyl)propane, 1,1,3-tris-(5-tert.butyl-4-hydroxy-2-methylphenyl)butane, 2,2-bis(5-tert.butyl-4-hydroxy-2-methylphenyl)-4-n-dodecylmercaptobutane, 1,1,5,5-tetra(5-tert.butyl-4-hydroxy-2-methylphenyl)pentane and ethylene glycol bis[3,3-bis(3'-tert.butyl-4'-hydroxyphenyl)butyrate].

O-, N- and S-benzyl compounds, such as, for example, 3,5,3',5'-tetra-tert.butyl-4,4'-dihydroxydibenzyl-ether, 4-hydroxy-3,5-dimethylbenzyl-mercaptoacetic acid octadecyl ester, tri(3,5-di-tert.butyl-4-hydroxybenzyl)amine, and bis(4-tert.butyl-3-hydroxy-2,6-dimethylbnezyl)dithiolterephthalate.

Hydroxybenzylated malonic esters, such as, for example, 2,2-bis(3,5-di-tert.butyl-2-hydroxybenzyl)malonic acid dioctadecyl ester, 2-(3-tert.butyl-4-hydroxy-5-methylbenzyl)malonic acid dioctadecyl ester, 2,2-bis(3,5-di-tert.butyl-4-hydroxybenzyl)malonic acid di-dodecylmercaptoethyl ester and 2,2-bis(3,5-di-tert.butyl-4-hydroxybenzyl)malonic acid di(4-tert.octylphenyl)ester.

Hydroxybenzyl-aromatics, such as, for example, 1,3,5-tri(3,5-di-tert.butyl-4-hydroxybenzyl)-2,4,6-trimethylbenzene, 1,4-di(3,5-di-tert.butyl-4-hydroxybenzyl)-2,3,5,6-tetramethylbenzene and 2,4,6-tri-(3,5-di-tert.butyl-4-hydroxybenzyl)phenol.

s-Triazine compounds, such as, for example, 2,4-bis-octylmercapto-6-(3,5-di-tert.butyl-4-hydroxyanilino)-s-triazine, 2-octylmercapto-4,6-bis(3,5-di-tert.butyl-4-hydroxyanilino)-s-triazine, 2-octylmercapto-4,6-bis(3,5-di-tert.butyl-4-hydroxyphenoxy)-s-triazine, 2,4,6-tris(3,5-di-tert.butyl-4-hydroxyphenoxy)-s-triazine, 2,4,6-tris(3,5-di-tert.butyl-4-hydroxyphenylethyl)-s-triazine and 1,3,5-tris-(3,5-di-tert.butyl-4-hydroxybenzyl)isocyanurate.

Amides of 3,5-di-tert.butyl-4-hydroxyphenylpropionic acid, such as, for example, 1,3,5-tris(3,5-di-tert.butyl-4-hydroxyphenyl-propionyl)-hexahydro-s-triazine and N,N'-bis(3,5-di-tert.butyl-4-hydroxyphenyl-propionyl)hexamethylenediamine.

Esters of 3,5-di-tert.butyl-4-hydroxyphenylpropionic acid with monohydric or polyhydric alcohols, such as, for example, methanol, ethanol, octadecanol, 1,6-hexanediol; 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]octane.

Esters of 5-tert.butyl-4-hydroxy-3-methylphenyl-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

Esters of 3,5-di-tert.butyl-4-hydroxyphenylacetic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethylisocyanurate and 4-hydroxymethyl-1-phospha-2,6,7-tri-oxabicyclo[2,2,2]octane.

Acylaminophenols, such as, for example, N-(3,5-di-tert.butyl-4-hydroxyphenyl)stearic acid amide and N,N'-bis(3,5-di-tert.butyl-4-hydroxyphenyl)-thio-bis-acetamide.

Benzylphosphonates, such as, for example, 3,5-di-tert.butyl-4-hydroxybenzylphosphonic acid dimethyl ester, 3,5-di-tert.butyl-4-hydroxybenzylphosphonic acid diethyl ester, 3,5-di-tert.butyl-4-hydroxybenzyl-phosphonic acid dioctadecyl ester and 5-tert.butyl-4-hydroxy-3-methylbenzylphosphonic acid dioctadecyl ester.

Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, mono- and di-octyliminodibenzyl and polymerized 2,2,4-trimethyl-1,2-dihydroquinoline.

UV-absorbers and light protection agents 2-(2'-Hydroxyphenyl)-benztriazoles, such as, for example, the 5'-methyl-, 3',5'-di-tert.butyl-, 5'-tert.butyl-, 5'-(1,1,3,3-tetramethyl-butyl)-, 5-chloro-3',5'-di-tert.butyl-, 5-chloro-3'-tert.butyl-5'-methyl-, 3'-sec.butyl-5'-tert.butyl-, 3'-[α-methylbenzyl]-5'-methyl-, 3'-[α-methylbenzyl]-5'-methyl-5-chloro-, 4'-hydroxy-, 4'-methoxy-, 4'-oxtoxy-, 3',5'-di-tert.amyl-, 3'-methyl-5'-carbomethoxyethyl- or 5-chloro-3',5'-di-tert.amyl-derivatives.

2,4-Bis(2'-hydroxyphenyl)-6-alkyl-s-triazines, such as, for example, the 6-ethyl-, 6-undecyl- or 6-heptadecyl-derivatives.

2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivatives.

1,3-Bis(2'-hydroxy-benzoyl)benzenes, such as, for example, 1,3-bis(2'-hydroxy-4'-hexyloxy-benzoyl)-benzene, 1,3-bis(2'-hydroxy-4'-octoxy-benzoyl)-benzene and 1,3-bis(2'-hydroxy-4'-dodecyloxy-benzoyl)-benzene.

Esters of optionally substituted benzoic acids, such as, for example, phenyl salicylate, octylphenyl salicylate, di-benzoylresorcinol, bis(4-tert.butyl-benzoyl)-resorcinol, benzoyl-resorcinol, 3,5-di-tert.butyl-4-hydroxybenzoic acid 2,4-di-tert.butyl-phenyl ester, octadecyl ester or 2-methyl-4,6-di-tert.butylphenyl ester.

Acrylates, such as, for example, α-cyano-β,β-diphenyl-acrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2-methylindoline.

Nickel compounds, such as, for example, nickel complexes of 2,2'-thiobis(4-tert.ocylphenol), such as the 1:1 and 1:2 complex, optionally with other ligands such as n-butylamine, triethanolamine or N-cyclohexyl-diethanolamine, nickel complexes of bis(4-tert.octylphenyl)sulphone, such as the 2:1 complex, optionally with other ligands such as 2-ethyl-carproic acid, nickel dibutyldithiocarbamate, nickel salts of 4-hydroxy-3,5-di-tert.butylbenzyl-phosphonic acid monoalkyl esters, such as the methyl, ethyl or butyl ester, the nickel complex of 2-hydroxy-4-methyl-phenyl-undecyl-ketonoxime and nickel 3,5-di-tert.butyl-4-hydroxybenzoate.

Oxalic acid diamides, such as, for example, 4,4'-di-octyloxyoxanilide, 2,2'-dioctyloxy-5,5'-di-tert.-butyloxanilide, 2,2'-di-didecyloxy-5,5'-di-tert.-butyloxanilide, 2-ethoxy-5-tert.butyl-2'-ethyl-oxanilide, 2-ethoxy-2'-ethyl-oxanilide, N,N'-bis-(3-dimethylaminopropyl)oxalamide, mixtures of o- and p-methoxy and o- and p-ethoxy-di-substituted oxanilides and mixtures of 2-ethoxy-5-tert.butyl-2'-ethyloxanilide with 2-ethoxy-2'-ethyl-5',4'-di-tert.butyloxanilide.

Metal deactivators, such as, for example, oxanilide, isophthalic acid dihydrazide, sebacic acid bisphenylhydrazide, bis-benzylidene oxalic acid dihydrazide, N,N'-diacetyl-adipic acid dihydrazide, N,N'-bis-salicyloyl-oxalic acid dihydrazide, N,N'-bis-salicyloyl-hydrazine and N,N'-bis-(3,5-di-tert.butyl-4-hydroxyphenyl-propionyl)hydrazine.

Phosphites, such as, for example triphenylphosphite, di-phenyl alkyl-phosphites, phenyl dialkylphosphites, trinonylphenylphosphite, trialurylphosphite, tri-octadecylphosphite, 3,9-di-isodecyloxy-2,4,8,10-tetraoxa-3,9-diphospha-spiro[5.5]undecane and tris(4-hydroxy-3,5-di-tert.butylphenyl)phosphite.

Compounds which destroy peroxide, such as, for example, esters of β-thiodipropionic acid, e.g., the lauryl, stearyl, myristyl or tridecyl ester, salts of 2-mercaptobenzimidazole, e.g., the zinc salt, and diphenylthiourea.

Polyamide stabilizers, such as, for example, copper salts in combination with iodides and/or phosphorus compounds and salts of divalent manganes.

Basic co-stabilizers, such as, for example, polyvinylpyrrolidone, melamine, benzoguanamine, triallyl cyanurate, dicyandiamide, urea derivatives, hydrazine derivatives, amines, polyamides, polyurethanes and alkali metal salts and alkaline earth metal salts of higher staurated or unsaturated fatty acids, e.g., Ca stearate, Mg laurate, Na ricinoleate, K palmitate and Zn stearate.

PVC stabilizers, such as, for example, organic tin compounds, organic lead compounds and Ba/Cd salts of fatty acids.

Nucleating agents, such as, for example, 4-tert.-butylbenzoic acid, adipic acid and diphenylacetic acid.

Other additives, such as, for example, plasticizers, lubricants, e.g., glycerine monostearate, emulsifiers, antistatic agents, flameproofing agents, pigments, carbon black, asbestos, glass fibres, kaolin and talc.

If the conventional additives are to be employed, it is preferable to use them in a weight ratio of 0.5 – 3 : 1 with respect to the stabilizing compound of this invention.

The following examples are given solely for the purpose of illustrating the present invention.

Examples 1 through 3 describe the preparation of the stabilizing compounds (I), (II), (III) or (IV) of this invention. Examples 4 through 11 describe the stabilizing effects of the stabilizing compounds of this invention against photo- and thermal-deterioration of various synthetic polymers.

EXAMPLE 1.

1,2-Bis(4-benzoyloxy-2,2,6,6-tetramethyl-puperidino)ethane

A mixture of 3 g. of 4-benzoyloxy-2,2,6,6-tetramethyl-piperidine and 5 g. of 1,2-dibromoethane was heated under reflux for 4 hours. After cooling, an 10% aqueous solution of potassium carbonate was added to the reaction mixture and the resulting mixture was extracted with benzene. The benzene extract was washed with a saturated aqueous solution of sodium chloride, dried and the benzene was distilled off. Crystalline residue was washed with petroleum benzine and recrystallized from dimethylformamide to give the desired product as white crystals with a decomposition point of 251°– 253°C.

Analysis for $C_{34}H_{48}N_2O_4$: Calculated: C,74.41%; H,8.82%; N,5.11% Found: C,74.18%; H,8.77%; N,5.32% IR spectrum (nujol mull): $\nu_{C=O}$ 1720 cm$^{-1}$ Substantially following the same procedure as set forth above, the following compounds were prepared.

1,6-Bis(4-benzoyloxy-2,2,6,6-tetramethyl-piperidino)-hexane m.p. 160° – 161°C.

1,4-Bis(4-benzoyloxy-2,2,6,6-tetramethyl-piperidino)-trans-2-butene m.p. 176° – 177°C.

2,2'-(4-benzoyloxy-2,2,6,6-tetramethylpiperidino)-p-xylene m.p. 143° – 144°C.

α, α'-bis(4-hydroxy-2,2,6,6-tetramethylpiperidino)-p-xylene m.p. 224° – 226°C.

EXAMPLE 2.

N,N'-Hexamethylene-bis(8-aza-7,7,9,9-tetramethyl-1,4-dioxa-spiro[4.5]decane)

To 6.2 g. of 8-aza-7,7,9,9-tetramethyl-1,4-dioxa-spiro[4.5]decane were added 3 g. of 1,6-dibromohexane, 6.8 g. of potassium carbonate and 10 ml. of kerosene and the resulting mixture was heated at 180°C for 12 hours. After cooling, ether was added to the reaction mixture and insolubles were filtered off from the mixture. The filtrate was concentrated, to the residue was added petroleum ether and crystalline substnaces were separated in situ by cooling. The substances so separated were recovered by filtration and recrystallized from n-hexane to give the desired product as white crystals melting at 164° – 165°C.

Analysis for $C_{28}H_{52}N_2O_4$: Calculated: C,69.95%; H,10.90%; N,5.83% Found: C,69.85%; H,10.91%; N,6.04%

Substantially following the same procedure as set forth above, the following compounds were prepared.

N,N'-octamethylene-bis(8-aza-7,7,9,9-tetramethyl-1,4-dioxa-spiro[4.5]decane) m.p. 112°– 113°C.

N,N'-decamethylene-bis(8-aza-7,7,9,9-tetramethyl-1,4-dioxa-spiro[4.5]decane) m.p. 98° – 99°C.

ethylene bis(8-aza-7,7,9,9-tetramethyl-1,4-dioxa-spiro[4.5]-8-decylacetate) m.p. 66° – 67°C.

N,N'-[terephthaloyl-bis(β-oxyethyl)]-bis(8-aza-7,7,9,9-tetramethyl-1,4-dioxa-spiro[4.5]decane) m.p. 226° – 227°C.

N,N'-hexamethylene-bis(8-aza-2-hydroxymethyl-7,7,9,9-tetramethyl-1,4-dioxa-spiro[4.5]decane) m.p. 165° – 166°C.

N,N'-(α,α'-p-xylene)-bis(9-aza-3,3,8,8,10,10-hexamethyl-1,5-dioxa-spiro[5.5]undecane) m.p. 205° – 206°C.

N,N'-ethylene-bis(9-aza-3-hydroxymethyl-3,8,8,10,10-pentamethyl-1,5-dioxa-spiro[5.5]undecane) m.p. 299° – 303°C.

N,N'-hexamethylene-bis(9-aza-3-hydroxymethyl-3,8,8,10,10-pentamethyl-1,5-dioxa-spiro[5.5]undecane) m.p. 225° – 226.5°C.

EXAMPLE 3.

1,6-Bis(2,2,6,6-tetramethyl-4-oxopiperidino)-hexane

In 5 ml. of ice-cooled 35 % aqueous hydrochloric acid was dissolved 100 mg. of N,N'-hexamethylene-bis(8-aza-7,7,9,9-tetramethyl-1,4-dioxa-spiro[4.5]decane) over about 10 minutes. The resulting solution was neutralized by the addition of an 10 % aqueous solution of sodium hydroxide and then extracted with n-hexane. From the hexane extract was distilled the solvent and the residue was recrystallized from petroleum ether to give the desired product as white crystals melting at 151° – 152°C.

Analysis for $C_{24}H_{44}N_2O_2$: Calculated: C,73.42%; H,11.30%; N,7.14% Found: C,73.42%; H,11.26%; N,7.21%

Substantially following the same procedure as set forth above, the following compounds were prepared.

1,8-Bis(2,2,6,6-tetramethyl-4-oxopiperidino)octane m.p. 96° – 97.5°C.

1,10-bis(2,2,6,6-tetramethyl-4-oxopiperidino)decane m.p. 69° – 71°C.

EXAMPLE 4.

Mixtures were made from 100 parts of polypropylene ("Noblen JHH-G", available from Nitsui Toatsu Chemicals Inc., Japan, employed after two recrystallizations from monochlorobenzene) and 0.25 part of each in turn of the stabilizing compounds of the invention indicated in Table I. The resulting mixtures were blended and melted, and the molten mixtures were moulded under heating and pressure into sheets 0.5 mm. thick. A control sheet, containing no stabilizer, was also made.

The sheets were exposed to ultraviolet irradiation at 45°C. in the "Standard Fade-Meter Type FA-1" manufactured and sold by Toyo Rika Instruments, Inc., Japan (a modification of the Atlas "Fade-O-meter" Type FDA-R which meets the requirements prescribed in paragraph 3.8 of Japanese Industrial Standard L-1044). The time taken for each sheet to become brittle is shown in Table I.

EXAMPLE 5.

Mixtures were made from 100 parts of high-density polyethylene ("Hi-Zex", available from Mitsui Toatsu Chemicals, Inc., Japan, employed after two recrystallizations from toluene) and 0.25 part of each in turn of the stabilizing compounds of the invneiton indicated in Table I. The resulting mixtures were made into sheets, in the same way as in Example 4; and a control sheet was also made, containing no stabilizer.

The brittleness time of each sheet was measured by the same test method as in Example 4.

The results are given in Table I.

Table I.

| Stabilizer Compound No. | Brittleness time (hours) | |
|---|---|---|
| | Polypropylene | High density polyethylene |
| 1 | 560 | 1100 |
| 2 | 480 | 980 |

Table I.-continued

| Stabilizer Compound No. | Brittleness time (hours) | |
| --- | --- | --- |
| | Polypropylene | High density polyethylene |
| 3 | 680 | 1360 |
| 4 | 440 | 900 |
| 5 | 580 | 1220 |
| 7 | 360 | 700 |
| 8 | 320 | 680 |
| 9 | 460 | 840 |
| 11 | 420 | 780 |
| 12 | 400 | 720 |
| 14 | 680 | 1420 |
| 19 | 920 | 1780 |
| 20 | 1040 | 1940 |
| 24 | 980 | 1900 |
| 31 | 1020 | 1960 |
| 37 | 620 | 1320 |
| 40 | 880 | 1700 |
| None | 60 | 400 |

EXAMPLE 6.

Mixtures were made from 100 parts of polystyrene ["Styron", trade name, employed after recytstallization from a mixture of benzene with methanol, available from Asahi-Dow Limited, Japan] and 0.25 part of each in turn of the stabilizing compounds of this invention as indicated in Table II. The resulting mixtures were molded at 180°C. under pressure into a plate with thickness of 1 mm. A control sheet, containing no stabilizer, was also made.

The plate thus formed was subjected to the exposure of ultraviolet ray irradiation in the Fade Meter as specified in the above Example 4 at 45°C. for 500 hours. A test piece of the treated plate was tested for color difference by means of a color-difference colorimeter according to the method prescribed in Japanese Industrial Standard "K-7103", and a change of the yellowness index of the plate was calculated according to the following equation:

$$\Delta YI = YI - YI_0$$

wherein $\Delta YI$ means a change of yellowness index, $YI$ means a yellowness index after exposure and $YI_0$ means an initial yellowness index of a test piece.

The results are summarized in the following Table II.

Table II.

| Stabilizer Compound No. | $YI_0$ | $\Delta YI$ |
| --- | --- | --- |
| 1 | 4.8 | + 6.9 |
| 3 | 4.6 | + 6.2 |
| 5 | 5.1 | + 6.3 |
| 19 | 4.5 | + 5.7 |
| 24 | 4.6 | + 5.3 |
| 30 | 4.9 | + 5.8 |
| 40 | 5.7 | + 6.3 |
| None | 4.3 | +17.0 |

EXAMPLE 7.

Mixtures were made from 100 parts of ABS resin ["Kane Ace B-12", trade name, available from Kanegafuchi Spinning Co., Ltd.] and 0.5 part of each in turn of the stabilizing compounds of this invention as indicated in Table III, the resulting mixture was kneaded on a kneading roll at 160°C. for 6 minutes and then molded into a sheet with a thickness of about 0.5 mm. a control sheet, containing no stabilizer, was also made.

The sheet thus formed was aged under the following aging condition and retentions of elongation and of tensile strength as well as coloration degree were determined by a conventional method.

Aging test

1. Exposure for 50 hours to the Sunshine Weather Meter prescribed in Japanese Industrial Standard JIS Z-0230 entitled "Accelerated Weathering Test of Rust Proofing Oils", Paragraph 2.

2. Aging at 190°C. for 30 minutes in a Geer's aging tester prescribed in Japanese Industrial Standard JIS K-6301 entitled "Physical Testing Methods for Vulcanized Rubber", Paragraph 6.5.

The results are given in the following Table III.

Table III.

| Stabilizer Compound No. | Weather Meter | | Geer's aging tester Discoloration |
| --- | --- | --- | --- |
| | Retention of elongation (%) | Retention of tensile strength (%) | |
| 1 | 68 | 79 | Pale brown |
| 3 | 74 | 78 | " |
| 5 | 75 | 82 | " |
| 19 | 77 | 81 | " |
| 24 | 78 | 83 | " |
| 30 | 75 | 80 | " |
| None | 54 | 71 | Brown |

EXAMPLE 8.

Mixtures were made from 100 parts of nylon-6 ("CM 1011", available from Toray Industries Inc., Japan) and 0.25 part of each in turn of the stabilizing compounds of the invention indicated in Table IV. The resulting mixtures were melted and moulded under pressure into films 0.1 mm. thick, by means of a conventional compressionmoulding machine. A control film, containing no stabilizer, was also made.

The films thus formed were aged under the aging condition as shown below and subjected to a tensile test to determine their retentions of elongation and of tensile strength by a conventional method.

Aging conditions

1. Exposure for 200 hours to ultraviolet irradiation at 45°C. in the Fade-Meter.

2. Aging at 160°C. for 2 hours in the Geer's aging tester.

The results are shown in Table IV.

Table IV.

| Stabilizer Compound No. | Fade-Meter | | Geer's aging tester | |
| --- | --- | --- | --- | --- |
| | Retention of elongation (%) | Retention of tensile strength (%) | Retention of elongation (%) | Retention of tensile strength (%) |
| 1 | 72 | 78 | 63 | 65 |
| 3 | 77 | 76 | 64 | 66 |
| 19 | 74 | 75 | 60 | 62 |
| 30 | 71 | 73 | 59 | 63 |
| None | 23 | 51 | 27 | 55 |

EXAMPLE 9.

Mixtures were made from 100 parts of polyurethane prepared from polycarprolactone ("E-5080", available from The Nippon Elastollan Industries Ltd., Japan) and 0.5 part of each in turn of the stabilizing compounds of the invention indicated in Table V. The resulting mixture were melted and moulded into sheets about 0.5 mm. thick. A control sheet, containing no stabilizer, was also made.

The sheets thus formed were exposed to ultraviolet irradiation for 15 hours at 45°C. in the Fade Meter described in Example 4 and their retention of elongation and tensile strength were then measured. The results are given in Table V.

Table V.

| Stabilizer Compound No. | Retention of elongation (%) | Retention of tensile strength (%) |
| --- | --- | --- |
| 1 | 85 | 79 |
| 3 | 88 | 81 |
| 19 | 89 | 85 |
| 40 | 83 | 76 |
| None | 78 | 52 |

EXAMPLE 10.

Mixtures were made from 100 parts of polyvinyl chloride ("Geon 103 EP", Available from The Japanese Geon Co., Ltd., Japan), 40 parts of dicotyl phthalate and 0.2 part of each in turn of the stabilizing compounds of the invention indicated in Table VI. The resulting mixture were kneaded for 5 minutes on kneading rolls at 140°C., and formed into sheets about 1 mm. thick. A control sheet, containing none of the stabilizers of the invention, was also made.

The sheets thus formed were aged under the conditions described below, and the degree of discoloration was noted.

Aging conditions

1. Exposure for 200 hours in the Sunshine Weather Meter.
2. Aging at 160°C. for 30 minutes in the Geer's aging tester.

The results are shown in Table VI.

Table VI.

| Stabilizer Compound No. | Weather Meter | Geer's aging tester |
| --- | --- | --- |
| 1 | Pale brown | Pale reddish brown |
| 3 | '' | '' |
| 5 | '' | '' |
| 19 | '' | '' |
| 31 | '' | '' |
| None | Brown | Reddish brown |

EXAMPLE 11.

Mixtures were made from 100 parts of polyester resin ["Ester-G 13", trade name, available from Mitsui Toatsu Chemicals, Inc., Japan], 1 part of benzoyl peroxide and 0.2 part of each in turn of the stabilizing compounds as indicated in Table VII. The resulting mixture was cured by pre-heating at 60°C. for 30 minutes and then heating at 100°C. for additional 1 hour to formed into a plate with a thickness of 3 mm. A control plate, containing no stabilizer, was also made.

The plate thus formed was exposed to irradiation in the Sunshine Weather Meter as described in the above Example 10 for 60 hours and the change of yellowness index thereof was determined according to the method described in the above Example 6.

The results are given in the following Table VII.

Table VII.

| Stabilizer Compound No. | $YI_0$ | $\Delta YI$ |
| --- | --- | --- |
| 1 | 2.3 | + 7.5 |
| 3 | 2.4 | + 7.8 |
| 5 | 2.4 | + 8.4 |
| 24 | 2.6 | + 8.5 |
| None | 1.9 | +13.8 |

It will be apparent from the above results that the piperidine derivatives (I), (II), (III) and (IV) of this invention are highly effective against photo- and thermal-deterioration of various synthetic polymers.

What is claimed is:

1. A synthetic polymer composition stabilized against photo- and thermal-deterioration wherein there is incorporated, in a sufficient amount to prevent said deterioration, at least one compound selected from the group consisting of the compounds having the formula

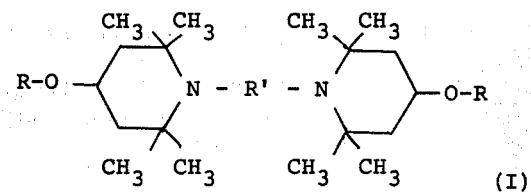

(I)

wherein
R' represents an alkylene group which may be interrupted with an oxygen or sulfur atom, an alkenylene group, an alkynylene group, an aralkylene group, an aliphatic diacyl group, a group of the formula

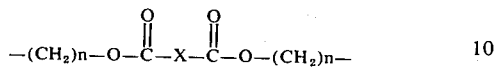

in which $n$ is an integer of 1 or 2 and X is an alkylene group, or o-, m- or p-phenylene group or the carbon atoms of CO groups may be directly joined in the absence of X or a group of the formula

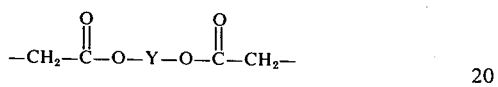

in which Y is an alkylene group or o-, m- or p-phenylene group; and

R represents hydrogen atom, an alkyl group, a cycloalkyl group, an aralkyl group, an aryl group, an alkoxycarbonylalkenyl group, an aliphatic, aromatic or heterocyclic monoacyl group, a N-substituted carbamoyl group, a N-substituted thiocarbamoyl group or a monovalent radical derived from an oxoacid, the compounds having the formula

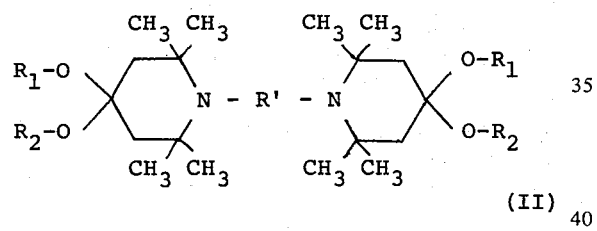

(II)

wherein
R' represents an alkylene group which may be interrupted with an oxygen or sulfur atom, an alkenylene group, an alkynylene group, an aralkylene group, an aliphatic diacyl group, a group of the formula

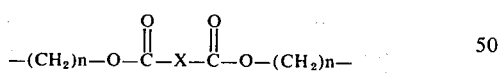

in which n is an integer of 1 or 2 and X is an alkylene group, or o-, m- or p-phenylene group or the carbon atoms of CO groups may be directly joined in the absence of X or a group of the formula

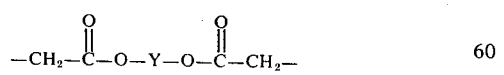

in which Y is an alkylene group or o-, m- or p-phenylene group;

$R_1$ and $R_2$ individually represent a lower alkyl group or they jointly represent, together with the oxygen atoms, a group of the formula

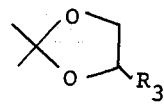

in which $R_3$ is hydrogen atom, a lower alkyl group or hydroxymethyl or a group of the formula

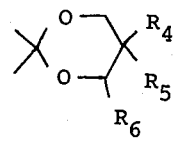

in which $R_4$ and $R_5$ may be the same or different and each represents hydrogen atom, a lower alkyl group or hydroxymethyl group and $R_6$ is hydrogen or a lower alkyl group, the compounds having the formula

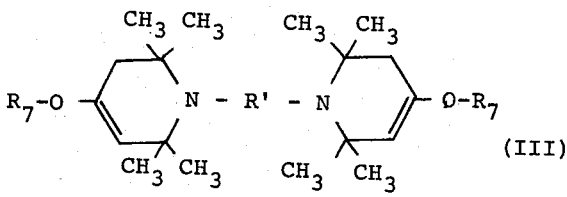

(III)

wherein
R' represents an alkylene group which may be interrupted with an oxygen or sulfur atom, an alkenylene group, an alkynylene group, an aralkylene group, an aliphatic diacyl group, a group of the formula

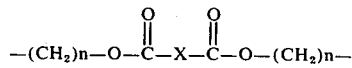

in which $n$ is an integer of 1 or 2 and X is an alkylene group, or o-, m- or p-phenylene group or the carbon atoms of CO groups may be directly joined in the absence of X or a group of the formula

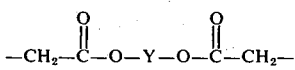

in which Y is an alkylene group or o-, m- or p-phenylene group; and $R_7$ represents an alkyl group or an aralkyl group, and the compounds having the formula

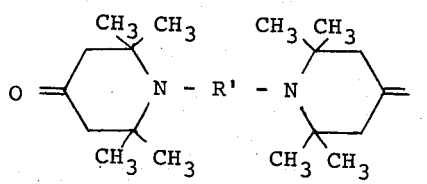

(IV)

wherein
R' represents an alkylene group which may be interrupted with an oxygen or sulfur atom, an alkenylene group, an alkynylene group, an aralkylene group, an aliphatic diacyl group, a group of the formula

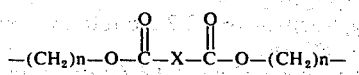

in which n is an integer of 1 or 2 and X is an alkylene group, or o-, m- or p-phenylene group or the carbon atoms of CO groups may be directly joined in the absence of X or a group of the formula

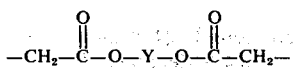

in which Y is an alkylene group or o-, m- or p- phenylene group.

2. The synthetic polymer composition according to claim 1 wherein said compound is selected from the compounds of the formula (I) wherein R' is an alkylene group of 1 to 6 carbon atoms which may be interrupted with an oxygen or sulfur atom, an alkenylene group of 2 or 4 carbon atoms, an aralkylene group of 1 to 6 carbon atoms in the alkylene moiety, a group of the formula

in which n is an integer of 1 or 2 and X is an alkylene group of 1 to 6 carbon atoms or o-, m- or p-phenylene group or the carbon atoms of CO groups may be directly joined in the absence of X or a group of the formula

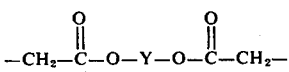

in which Y is an alkylene group of 1 to 6 carbon atoms or o-, m- or p-phenylene group; and R is hydrogen atom, an alkyl group of 1 to 18 carbon atoms, an alkoxycarbonylalkenyl group of 1 to 3 carbon atoms in the alkoxy moiety and of 2 to 4 carbon atoms in the alkenyl moiety, an aliphatic acyl group of 2 to 18 carbon atoms or a benzoyl group which may be substituted with halogen, hydroxy or alkyl of 1 to 3 carbon atoms.

3. The synthetic polymer composition according to claim 1 wherein said compound is selected from the compounds of the formula (II) wherein R' is an alkylene group of 1 to 6 carbon atoms which may be interrupted with an oxygen or sulfur atom, an alkenylene group of 2 to 4 carbon atoms, an aralkylene group of 1 to 6 carbon atoms in the alkylene moiety, a group of the formula

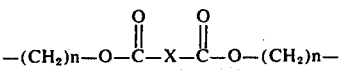

in which n is an integer of 1 or 2 and X is an alkylene group of 1 to 6 carbon atoms or o-, m- or p-phenylene group or the carbon atoms of CO groups may be directly joined in the absence of X or a group of the formula

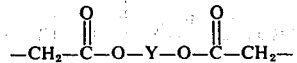

in which Y is an alkylene group of 1 to 6 carbon atoms or o-, m- or p-phenylene group; and $R_1$ and $R_2$ individually represent an alkyl group of 1 to 4 carbon atoms or they jointly represent, together with the oxygen atoms, a group of the formula

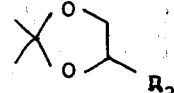

in which $R_3$ is hydrogen atom, an alkyl group of 1 to 4 carbon atoms or hydroxymethyl group or a group of the formula

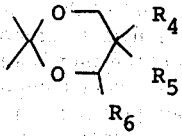

in which $R_4$ and $R_5$ individually represent hydrogen atom, an alkyl group of 1 to 4 carbon atoms or hydroxymethyl group provided that when one of $R_4$ and $R_5$ is hydroxymethyl group, the other is hydrogen atom or an alkyl group of 1 to 4 carbon atoms and $R_6$ is hydrogen atom.

4. The synthetic polymer composition according to claim 1 wherein said compound is selected from the compounds of the formula (III) wherein R' is an alkylene group of 1 to 6 carbon atoms which may be interrupted with an oxygen or sulfur atom, an alkenylene group of 2 to 4 carbon atoms, an aralkylene group of 1 to 6 carbon atoms in the alkylene moiety, a group of the formula

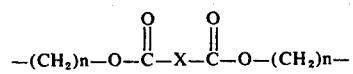

in which n is an integer of 1 or 2 and X is an alkylene group of 1 to 6 carbon atoms or o-, m- or p-phenylene group or the carbon atoms of CO groups may be directly joined in the absence of X or a group of the formula

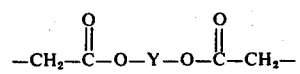

in which Y is an alkylene group of 1 to 6 carbon atoms or o-, m- or p-phenylene group; and $R_7$ is an alkyl group of 1 to 18 carbon atoms or a phenylalkyl group of 1 or 2 carbon atoms in the alkyl moiety.

5. The synthetic polymer composition according to claim 1 wherein said compound is selected from the compounds of the formula (IV) wherein R' is an alkylene group of 1 to 6 carbon atoms which may be interrupted with an oxygen or sulfur atom, an alkylene group of 2 to 4 carbon atoms, an aralkylene group of 1 to 6 carbon atoms in the alkylene moiety, a group of the formula

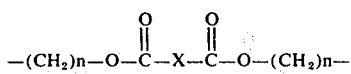

in which n is an integer of 1 or 2 and X is an alkylene group of 1 to 6 carbon atoms or o, m- or p-phenylene group or the carbon atoms of CO groups may be directly joined in the absence of X or a group of the formula

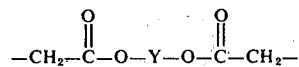

in which Y is an alkylene group of 1 to 6 carbon atoms or o-, m- or p-phenylene group.

6. The synthetic polymer composition according to claim 1 wherein said compound (I), (II), (III) or (IV) is incorporated in an amount of 0.01 – 5.0% by weight, based upon the amount of the synthetic polymer.

7. The synthetic polymer composition according to claim 1 wherein said polymer is a polyolefin.

8. The synthetic polymer composition according to claim 1 wherein said polymer is a polyvinyl chloride.

9. The synthetic polymer composition according to claim 1 wherein said polymer is a polyurethane.

10. The synthetic polymer composition according to claim 1 wherein said polymer is a polyester.

11. The synthetic polymer composition according to claim 1 wherein said polymer is an acrylonitrile-styrene-butadiene copolymer.

12. The synthetic polymer composition according to claim 1 wherein said compound is selected from the group consisting of
1,2-bis(4-benzoyloxy-2,2,6,6-tetramethylpiperidino)ethane,
α,α'-bis(4-benzoyloxy-2,2,6,6-tetramethylpiperidino)-p-xylene,
2,2'-bis(2,2,6,6-tetramethyl-4-stearoyloxypiperidino)diethylether,
1,4-bis(4-benzoyloxy-2,2,6,6-tetramethylpiperidino)-trans-2-butene,
α,α'-bis(4-hydroxy-2,2,6,6-tetramethylpiperi-dino)-p-xylene,
N,N'-hexamethylene-bis(8-aza-7,7,9,9-tetra-methyl-1,4-dioxa-spiro[4.5]decane),
ethylene bis(8-aza-7,7,9,9-tetramethyl-1,4-dioxa-spiro[4.5]-8-decylacetate),
N,N'-[terephthaloyl-bis(β-oxyethyl)]-bis(8-aza-7,7,9,9-tetramethyl-1,4-dioxa-spiro[4.5]-decane),
N,N'-hexamethylene-bis(8-aza-2-hydroxymethyl-7,7,9,9-tetramethyl-1,4-dioxa-spiro[4.5]-decane),
N,N'-(α,α'-p-xylylene)-bis(9-aza-3,3,8,8,10,10-hexamethyl-1,5-dioxa-spiro[5.5]undecane) and
1,6-bis(2,2,6,6-tetramethyl-4-oxopiperidino)-hexane.

* * * * *